US00PP14418P29

(12) United States Plant Patent
Magee

(10) Patent No.: US PP14,418 P2
(45) Date of Patent: Dec. 23, 2003

(54) ILEX HYBRID PLANT NAMED 'MAGIANA'

(50) Latin Name: *(Ilex cornuta×Ilex pernyi)×Ilex latifolia*
Varietal Denomination: Magiana

(75) Inventor: Jack Mitchell Magee, Poplarville, MS (US)

(73) Assignee: Plant Development Services Inc., Laxley, AL (US)

( * ) Notice: Subject to any disclaimer, the term of this patent is extended or adjusted under 35 U.S.C. 154(b) by 0 days.

(21) Appl. No.: 10/201,803

(22) Filed: Jul. 25, 2002

(51) Int. Cl.[7] ..... A01H 5/00
(52) U.S. Cl. ..... Plt./247
(58) Field of Search ..... Plt./247

*Primary Examiner*—Kent Bell

(57) ABSTRACT

A new and distinct variety of Ilex plant found as an openly pollinated seedling of Ilex hybrid 'Mary Nell'. The new variety possesses a dense, upright, pyramidal growth habit, attractive orange-red fruit, glossy dark green foliage, and distinctly arranged leaf serrations.

1 Drawing Sheet

Genus species: (*Ilex cornuta×Ilex pernyi*)×*Ilex latifolia*.
Varietal denomination: 'Magiana'.

BACKGROUND OF THE INVENTION

This new Ilex variety named 'Magiana' was found as a plant within the progeny of a controlled open pollination of Ilex hybrid 'Mary Nell', an unpatented variety, maintained in the Evergreen Nursery at Poplarville, Miss. The seedling was discovered by Jack Mitchell Magee in May, 1989. The new and distinct Ilex hybrid plant of this invention comprises a novel and valuable holly plant with a dense, upright, pyramidal shape, attractive orange-red fruit, and unusual leaf serrations. As with the parent plant, the plant of this invention may be advantageously employed as a specimen appointment, in either formal or informal groupings, and is very attractive in mass plantings. The plant serves well in foundation plantings and is adapted for culture as a potted plant. This plant is responsive to pruning and training and may be used in forming attractive hedges and maintained without an excessive amount of care.

Asexual propagation of the new plant by cuttings has been under Mr. Magee's direction at the same location. The new plant retains its distinctive characteristics and reproduces true to type in successive generations. The plant cannot be reproduced true from seed.

SUMMARY OF THE INVENTION

The following are the most outstanding and distinguishing characteristics of this new cultivar when grown under normal horticultural practices in Poplarville, Miss.

1. Dense, upright, and pyramidal in nature.
2. Hardy to Zone 7.
3. Heat and drought tolerant.
4. Fast growth rate under normal fertilization and moisture conditions.
5. Tolerates most soils from moist to dry and from sand to clay.
6. Relatively past resistant.
7. Very desirable in planters.
8. Makes a good hedge or screen.

9. Easy to root from cuttings collected any time of year.
10. Produces attractive orange-red fruit in the fall which persist into the winter and which may result in bird visitations.
11. Has the ability to be sheared and trimmed to be kept within prescribed limits.
12. Mature leaves are a glossy rich green color with attractive spines.
13. Easily trained into a small tree.

DESCRIPTION OF THE DRAWINGS

This new Ilex hybrid variety is illustrated by the accompanying photographic prints in which:

1. The photograph at the top of the sheet is a close-up view of the attractive orange-red fruit and mature foliage of the new variety.
2. The photograph at the bottom of the sheet is a side-by-side photograph of (from left to right) Ilex hybrid 'Magiana', Ilex hybrid 'Mary Nell' and Ilex hybrid 'Conot' U.S. Plant Pat. No. 12,010. The photograph, which was taken in late winter, shows the new variety's dense, upright, and pyramidal growth habit.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Descriptions of colors in ordinary terms are presented where appropriate for clarity in meaning.

BOTANICAL DESCRIPTION OF THE PLANT

The following is a detailed description of the new variety of Ilex based on my observations made of 2 year old plants grown in 3 gallon containers in wholesale commercial production practices, in greenhouses, and in established landscape plantings in Poplarville, Miss.

DISTINCTIVE CHARACTERISTICS

TABLE 1

| Characteristic | Ilex hybrid 'Maglana' | Ilex hybrid 'Mary Nell' | Ilex hybrid 'Conot' PP#12,010 |
|---|---|---|---|
| Height (Mature) | 15–20' | 15–20' | 12–15' |
| Width (Mature) | 12–15' | 12–15' | 8–10' |
| Leaf Length | 1 ¾–2 ½" | 2 ⅝–3 ½" | 1 ½–2 ¼" |
| Leaf Width | 1–1 ½" | 1 ⅛–1 ¾" | ⅞–1 ⅜" |
| Internode Length | ¼–½" | ⅝–1 ¼" | ½–¾" |
| Leaf Glossiness (Mature) | Glossy | Very Glossy | Glossy |
| Leaf Shape | Elliptic to elliptic lanceolate | Ovate to broadly lanceolate | Elliptic to elliptic lanceolate |
| Leaf Spines (Pairs) | 6–9 | 9–11 | 6–9 |
| Fruit Color | Orange-Red G. 33A | Red G. 40A | Orange-Red G. 33A |
| Fruit Size | ¼–⅜" | ⅜–7/16" | ¼–⅜" |
| Fruit Set | Moderate | Heavy | Heavy |
| Mature Shape | Dense, upright, pyramidal | Upright, pyramidal | Dense upright, pyramidal. |

The parent plant of the new variety 'Magiana' is Ilex hybrid 'Mary Nell' (unpatented) which originated from a controlled cross made in 1962 by Joe McDaniel in Semmes, Ala. The female parent was *Ilex cornuta*×*Ilex pernyi* 'Red Delight' (unpatented), named and introduced by Henry Hohman in Kingsville, Md. The male parent was *Ilex latifolia*. Ilex hybrid 'Mary Nell' was named in 1981 by Thomas H. Dodd, Jr. after Joe McDaniel's wife.

Ilex hybrid 'Conot' U.S. Plant Pat. No. 12,010 is another selected seedling of Ilex hybrid 'Mary Nell'. This patented plant is comparable to the new plant; however, there are many differences, the most obvious being the growth rate, foliage size, and fruit set.

Classification:
Botanical: (*Ilex cornuta*×*Ilex pernyi*)×*Ilex latifolia*.
Form: Dense, upright, and pyramidal.
Height: 15–20'.
Width: 12–15'.
Growth habit: Shrub or small tree.
Growth rate: Fast under normal fertilization and moisture conditions. Reaches mature height of 15 to 20 feet and width of 12 to 15 feet in 8 to 10 years.
Foliage: Alternate, simple, evergreen, elliptic to elliptic lanceolate, and varying in size from 1¾" to 2½" long and 1" to 1½" wide. The margins are slightly convex and serrate with 6 to 9 pairs of prominent spines.

The spines vary in length and width from 1/16 to ⅜". The apex is acute and triangular with 3 prominent spines. The terminal spine is slightly larger than the next pair and points downward at an angle to the main leaf blade. Spines alternate between long and short after this first pair. The base of the leaf is obtuse. The petiole is 3/16 to ¼" long with a 1/16" to 3/32" diameter. Mid-veins and laterals are slightly impressed on the upper leaf surface and the mid-veins are prominent on the underside. Immature mid and lateral veins are Yellow-Green Group 144B top and bottom and mature to Yellow-Green Group 146D. The upper surface of the immature leaf is glossy, glabrous, and is Yellow-Green Group 144A. The lower surface of the immature leaf is Yellow-Green Group 144A and matte. As the leaves mature the upper surface becomes closest to Green Group 139A and the lower leaf surface becomes Yellow-Green Group 146C. This mature leaf color persists throughout the winter. Although the mature leaf color of the new variety is closest to Green Group 139A, which is also the color of the parent plant, it appears to be a shade lighter when viewed in full sun. The degree of glossiness of the mature leaf is slightly less than that of the parent plant.

In 1994, the date of initial spring growth was March 14, in Poplarville, Miss. After the spring flush, there was almost continuous growth until fall, ending October 28, also in Poplarville, Miss. This growth pattern was identical to the parent plant. When grown in full sun, the internode length of this plant is ¼" to ½" compared to ⅝" to 1¼" for the parent plant. When grown in light shade, the internode length is ⅝" to ⅞". As would be expected, either plant grown in the shade results in a taller, less dense plant with larger leaves.

The average length of terminal growth of the initial spring flush is about 12" for a plant in full sun and about 14" when grown in shade. After this initial flush we normally trim the plant lightly and the plant then continues to grow about 8" until we trim it a second time in the early fall. The fall growth of about 10" then hides the cut limbs. We finish in the fall with a three gallon plant about 34" tall and 20" wide. I have not noticed a difference in vigor between this plant and the parent. In the landscape, little or no pruning is necessary to produce a dense and pyramidal shrub in full sun. In shade, however, some trimming may be needed to produce the same effect. The lower limbs can be removed to produce a small tree with attractive gray-brown bark.

Stems: The young shoots and petioles are Yellow-Green Group 144A, glabrous, and matte. After one or more years the stems are generally Grey-Brown Group 199C, glabrous and rugose. The pith is solid and uniform.
Flowers: Small, creamy yellow, inconspicuous, slightly fragrant, borne on previous season's growth from March to May. Flower structure of this plant is identical to that of the parent plant. Buds are globular, 1/16" to ⅛" in diameter, Yellow-Green Group 144A, and without foliaceous appendages. Flowers are clustered in the leaf axils and are 4-merous. Unbranched pedicels are about ¼" long and Yellow-Green Group 144A. The four ovate sepals are persistent, glabrous, 1/32" to 1/16" wide, 1/16" to 3/32" long, Yellow-Green Group 144A (upper and lower surfaces), and united at the base. The sepals have acute apices and entire margins. The four ovate petals are 1/16" to ⅛" wide, ⅛" to 3/16" long, Yellow Group 2D (upper and lower surfaces), arranged regularly, united at the base, and imbricate in bud. The petals have obtuse apices and entire margins. The ovary protrudes from the receptacle and is Green Group 143A. The ovary is devoid of styles and the stigma is discoid and lobed. There are four ⅛" long stamens with under-developed anthers which are White Group 155D. No pollen is produced. Blooms are small to medium in size, Yellow Group 2D, ⅜" in diameter, and last on the plant in the garden two to four days.
Fruit: Drupaceous, globose, ¼ to ⅜" diameter, borne fasciculate with two to five fruits on short unbranched pedicles ¼" long. Each fruit contains four pyrenes. Matures to Orange-Red Group 33A in mid-November in Poplarville, Miss. and persists into the winter. Normally, fruit set is moderate.
Culture: Grows well in a wide range of conditions and tolerates sun to part shade. Grows in nearly any soil type, from moist to very dry and sand to clay. Responds well to mulching and medium applications of fertilizer; prefers PH 5 to 6.5. Little pruning is needed. Can be sheared. Disease and pest resistance is comparable to Ilex hybrid 'Mary Nell'. Propagated with semi-hardwood cuttings any time of year. Cuttings taken in late spring initiate roots in 6 to 8 weeks and are well rooted in 4 to 5 months. The root system is fibrous and rapidly established.

I claim:

1. A new and distinct variety of Ilex plant named 'Magiana', as illustrated and described.

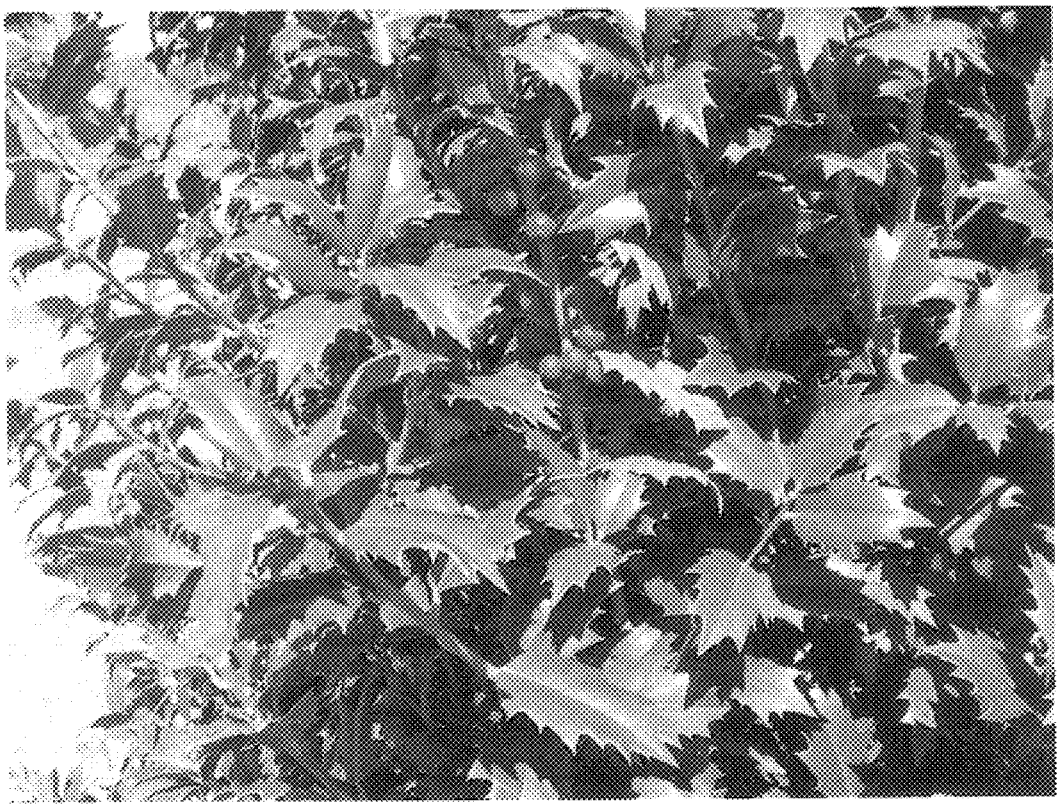
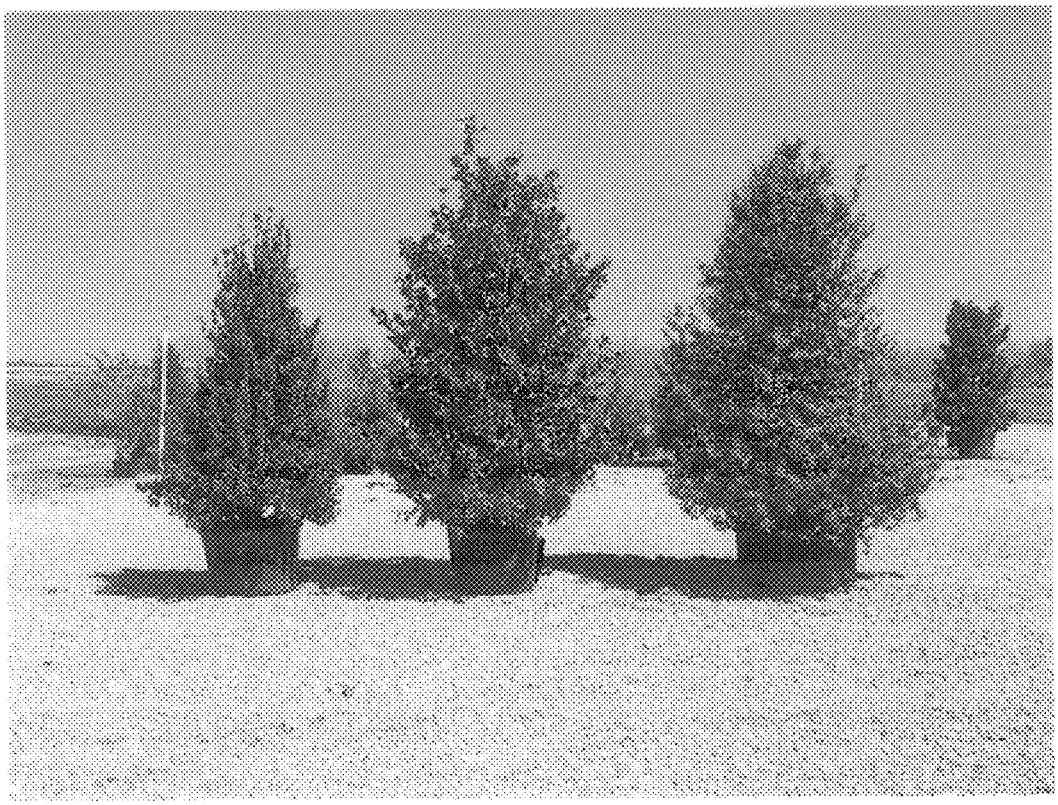

* * * * *